United States Patent
Benard et al.

(10) Patent No.: US 6,939,938 B2
(45) Date of Patent: *Sep. 6, 2005

(54) AMPHIPHILIC CATIONIC ASSOCIATIVE POLYMERS, PREPARATION PROCESS, USE AS THICKENERS AND COMPOSITION COMPRISING THEM

(75) Inventors: Sylvi Benard, Attainville (FR); Simon Trouille, Rantigny (FR); Mireille Arnaud-Roux, Aulnay sous Bois (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/347,414

(22) Filed: Jan. 21, 2003

(65) Prior Publication Data

US 2003/0166822 A1 Sep. 4, 2003

Related U.S. Application Data

(60) Provisional application No. 60/357,621, filed on Feb. 20, 2002.

(30) Foreign Application Priority Data

Jan. 21, 2002 (FR) ............................................. 02 00704

(51) Int. Cl.⁷ ............................................... C08G 18/66
(52) U.S. Cl. ............................ 528/49; 528/71; 524/591; 424/70.28; 424/78.03; 424/78.17
(58) Field of Search ........................... 528/49; 524/591; 424/70.28, 78.03, 78.17

(56) References Cited

U.S. PATENT DOCUMENTS

| | | | |
|---|---|---|---|
| 3,877,945 A | * | 4/1975 | Rosenhahn et al. .......... 430/518 |
| 4,110,286 A | | 8/1978 | Vandegaer et al. |
| 4,617,341 A | | 10/1986 | Laine et al. |
| 5,281,654 A | | 1/1994 | Eisenhart et al. |
| 2003/0124079 A1 | * | 7/2003 | Mougin et al. .......... 424/70.11 |

FOREIGN PATENT DOCUMENTS

| | | |
|---|---|---|
| EP | 0 978 522 | 2/2000 |
| EP | 1 174 450 | 1/2002 |

* cited by examiner

Primary Examiner—Rachel Gorr
(74) Attorney, Agent, or Firm—Finnegan, Henderson, Farabow, Garrett & Dunner, L.L.P.

(57) ABSTRACT

Novel water-soluble or water-dispersible amphiphilic cationic associative polymers, a process for preparing them and their use in compositions for topical application, such as for cosmetic use, as thickeners, and the compositions comprising these polymers.

56 Claims, No Drawings

AMPHIPHILIC CATIONIC ASSOCIATIVE POLYMERS, PREPARATION PROCESS, USE AS THICKENERS AND COMPOSITION COMPRISING THEM

This application claims benefit of U.S. Provisional Application No. 60/357,621, filed Feb. 20, 2002.

The present disclosure relates to novel water-soluble or water-dispersible amphiphilic cationic associative polymers, and also to their use in compositions for topical application, such as for cosmetic or therapeutic use.

As regards the polymers of the present disclosure, the term "water-soluble" means that these polymers have a solubility in water at room temperature (25° C.) of at least 1% by weight, i.e. up to this concentration, no precipitate may be detected by the naked eye, and the solution is visually clear and homogeneous.

As disclosed herein, "water-dispersible" polymers means polymers which, when suspended in water, spontaneously form globules with a mean size ranging, for example, from 5 nm to 600 nm, such as ranging from 5 nm to 500 nm, measured by light scattering using a Coulter machine.

The thickening and/or gelation of aqueous media with polymers has been a subject of research for a long time, especially in the cosmetics and pharmaceutical industries. Producing an advantageous thickening effect with a water-soluble polymer generally results in a high, molar mass and a large hydrodynamic volume. The gelation of an aqueous medium may be considered to be the result of a three-dimensional polymer network obtained by the crosslinking of linear polymers or by copolymerization of difunctional and polyfunctional monomers. The use of polymers with a very high molar mass, however, may pose a certain number of problems, such as a rather unpleasant texture and/or difficulty in spreading the gels obtained.

One approach consists in using, as a thickener, polymers capable of reversibly associating with each other or with other molecules or particles. This physical association can give rise to thixotropic or shear-thinning macromolecular systems, i.e. systems whose viscosity depends on the shear forces to which they are subjected.

Such polymers capable of reversibly associating with each other or with other molecules are known as associative polymers. The interaction forces involved may be of very different types, for example electrostatic type, hydrogen bonding type, or hydrophobic type.

One type of associative polymers is amphiphilic polymers, i.e. polymers comprising at least one hydrophilic portion that makes them water-soluble and at least one hydrophobic portion via which the polymers interact and assemble together or with other molecules.

Use of associative polymers, such as associative polyurethanes, is known in the cosmetics industry. However, the rheological and cosmetic properties of these polymers may not be optimal.

As disclosed herein, a novel family of water-soluble or water-dispersible cationic associative amphiphilic polymers has been discovered, the thickening qualities of, which may be improved compared with the prior art and which may have good cosmetic properties.

The thickening properties of the polymer as disclosed herein can allow it to be used in a reduced amount. This advantage can improve the texture of the composition comprising the polymer. The gel obtained by using the polymers as disclosed herein can have a pleasant feel and can spread easily.

In one embodiment, disclosed herein is at least one polymer of formula (I) below:

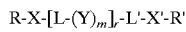

in which:
R and R', which may be identical or different, are chosen from hydrophobic groups and a hydrogen atom;
X and X', which may be identical or different, are chosen from groups comprising at least one amine functional group chosen from tertiary and quaternary amine functional groups, optionally bearing at least one hydrophobic group;
L and L', which may be identical or different, are chosen from groups derived from diisocyanate;
Y is chosen from hydrophilic groups;
r is an integer ranging, for example, from 1 to 100, such as from 1 to 50, and further such as from 1 to 25; and
m is a number ranging, for example, from 1 to 1,000, wherein the polymer comprises at least one amine functional group chosen from protonated and quaternized amine functional groups and at least one hydrophobic group, it being understood that the amount of the quaternized amine unit (or degree of quaternization) is at least 85%.

In another embodiment, disclosed herein is a process for preparing the at least one polymer above, in which a quaternized amine derivative is reacted with a diisocyanate prepolymer.

Further disclosed herein is the use of at least one polymer as defined above as a thickener.

Even further disclosed herein is a composition comprising the at least one polymer as defined above.

The term "polymer" means the novel associative polymers as disclosed herein and includes, for example, polyurethanes per se, polyureas, polythioureas, and the copolymers thereof.

The family of water-soluble or water-dispersible cationic amphiphilic associative polymers as disclosed herein may be represented by at least one polymer having formula (I) below:

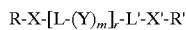

in which:
R and R', which may be identical or different, are chosen from hydrophobic groups and a hydrogen atom;
X and X', which may be identical or different, are chosen from groups comprising at least one amine functional group chosen from tertiary and quaternary amine functional groups, optionally bearing at least one hydrophobic group;
L and L', which may be identical or different, are chosen from groups derived from diisocyanate;
Y is chosen from hydrophilic groups;
r is an integer ranging, for example, from 1 to 100, such as from 1 to 50, and further such as from 1 to 25; and
m is a number ranging, for example, from 1 to 1,000,
wherein the at least one polymer comprises at least one amine functional group chosen from protonated and quaternized amine functional groups and at least one hydrophobic group,
it being understood that the amount of the quaternized amine unit is at least 85%.

In one embodiment of the cationic associative polymers as disclosed herein, the content of the quaternized amine unit ranges, for example, from 87% to 100%, and further such as from 88% to 99%.

The quaternized amine functional groups of the polymers can result from the quaternization of a tertiary amine with alkylating agents comprising at least one hydrophobic group, i.e., compounds of the type RQ or R'Q, in which R and R' are as defined above and Q is a leaving group, such as a halide or a sulphate.

The neutralized amine functional groups of the polymers can result from the neutralization of the tertiary amine. The neutralized amine functional groups may also result from the hydrolysis of excess isocyanate functional groups at the end of the chain, followed by alkylation of the primary amine functional groups formed, with alkylating agents comprising at least one hydrophobic group, i.e., compounds of the type RQ or R'Q, in which R and R' are as defined above and Q is a leaving group, such as a halide or a sulphate.

In one embodiment, the at least one polymer as disclosed herein corresponds to formula (I) above in which:

R and R', which may be identical or different, are chosen from hydrophobic groups, and X and X', which may be identical or different, are chosen from groups comprising at least one quaternary amine functional group.

The at least one hydrophobic group of the polymer as disclosed herein can result from the quaternization reaction; it can be introduced via the quaternizing agent.

The number-average molecular mass of the cationic amphiphilic associative polymers ranges, for example, from 10,000 to 60,000, such as from 15,000 to 55,000, and further such as from 20,000 to 50,000.

The term "hydrophobic group" means a group chosen from radicals and polymeric groups comprising at least one hydrocarbon-based chain chosen from linear and branched, saturated and unsaturated hydrocarbon-based chains, which optionally comprise at least one hetero atom, such as P, O, N and S, and radicals comprising at least one chain chosen from perfluoro and silicone chains. When the term "hydrophobic group" means a group chosen from hydrocarbon-based radicals, the hydrophobic group comprises at least 10 carbon atoms, such as from 10 to 30 carbon atoms, further such as from 12 to 30 carbon atoms, and even further such as from 18 to 30 carbon atoms. For example, this hydrophobic group may be a group chosen from linear and branched $C_{12}$–$C_{30}$ alkyl groups, such as decyl, dodecyl, myristyl, palmityl and stearyl groups.

In one embodiment, the hydrocarbon-based hydrophobic group is derived from a monofunctional compound. For example, the hydrophobic group may be provided by an alkylating agent, such as an ammonium halide or sulphate comprising a labile hydrogen, for example, an alcohol functional group, and a $C_{10-30}$ alkyl chain. The hydrophobic group may also be chosen from hydrocarbon-based polymeric groups, such as polybutadiene.

The groups X and X' can, for example, be chosen from one of the following formulae:

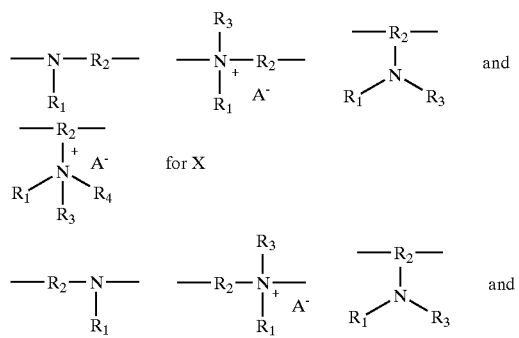

-continued

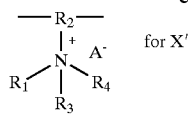

in which:

$R_2$ is a radical chosen from linear and branched alkylene radicals comprising from 1 to 20 carbon atoms, optionally comprising at least one ring chosen from saturated and unsaturated rings, and arylene radicals, wherein at least one of the carbon atoms in said radicals is optionally substituted with at least one hetero atom chosen from N, S, O and P; and $R_1$, $R_3$ and $R_4$, which may be identical or different, are chosen from linear and branched $C_1$–$C_{30}$ alkyl radicals, linear and branched alkenyl radicals, and aryl radicals, wherein at least one of the carbon atoms in said radicals is optionally substituted with at least one hetero atom chosen from N, S, O and P; and $A^-$ is chosen from physiologically-acceptable counter-ions.

The groups L and L' can, for example, represent a group of the following formula:

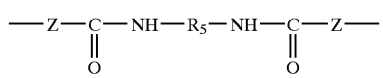

in which:

Z is a radical chosen from —O—, —S— and —NH—; and $R_5$ is a radical chosen from linear, branched and cyclic, saturated and unsaturated divalent alkylene radicals comprising from 1 to 20 carbon atoms, optionally comprising at least one hetero atom chosen from N, S, O and P.

With regard to the meaning of Y, the term "hydrophilic group" means a group chosen from polymeric and non-polymeric water-soluble groups. The hydrophilic group comprises at least one functional group comprising labile hydrogen, for example, at least two functional groups comprising labile hydrogen. These functional groups comprising labile hydrogen may be, for example, chosen from alcohol, primary amine, secondary amine, and thiol functional groups. This compound may be chosen from molecules and polymers terminated at the ends of the chains with one of these functional groups comprising labile hydrogen.

Non-limiting examples of non-polymeric water-soluble groups include ethylene glycols, diethylene glycols, and propylene glycols.

When, in one embodiment, the hydrophilic group is a polymeric group, non-limiting examples include polyethers, sulphonated polyesters, sulphonated polyamides, and a mixture of these polymers. The hydrophilic compound may, for example, be chosen from polyethers, such as poly(ethylene oxide) and poly(propylene oxide).

The cationic associative amphiphilic polymers as disclosed herein can generally be formed from diisocyanates and from various compounds that have at least one functional group comprising labile hydrogen. The functional groups comprising labile hydrogen may be, for example, chosen from alcohol, primary and secondary amine functional groups, and thiol functional groups, giving, after reaction with the diisocyanate functional groups, polyurethanes, polyureas and polythioureas, respectively.

The polymers as disclosed herein may, for example, be obtained according to a process in which a quaternized amine derivative is reacted with a diisocyanate prepolymer.

This process can, for example, make it possible to obtain a high degree of quaternization, since, for example, the quaternization yield is controlled and is made independent of the polymer's mass.

The "diisocyanate prepolymer" may be obtained by coupling a prepolymer having at least one functional group comprising labile hydrogen as defined above with a diisocyanate of the following formula:

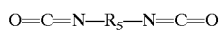

in which $R_5$ is as defined above.

The production of isocyanate ends may be controlled by means of the OH/NCO ratio. In one embodiment, the ratio is an excess of NCO.

Non-limiting examples of diisocyanates include methylenediphenyl diisocyanates, methylenedicyclohexyl diisocyanates, isophorone diisocyanates, toluene diisocyanates, naphthalene diisocyanates, butane diisocyanates and hexane diisocyanates.

The "quaternized amine derivative" is a compound comprising at least one unit comprising a quaternized amine functional group, and such as at least two units comprising an amine functional group. This compound, in one embodiment, comprises only one unit comprising an amine functional group. This compound also comprises at least one labile hydrogen atom, and such as at least two labile hydrogen atoms, borne, for example, by a functional group chosen from hydroxyl, primary amine, secondary amine and thiol functional groups. It is also possible to use a mixture of compounds chosen from monofunctional, difunctional and multifunctional compounds (one, two or more labile hydrogen atoms); however, the percentage of multifunctional compounds is, in one embodiment, small in the mixture. For example, the compound may be monofunctional (only one labile hydrogen).

"Quaternized amine derivatives" may, for example, include the product of a reaction between i) a compound chosen from N-methylethanolamines, N-methyldiethanolamines, N, N-dimethylethanolamines, N, N-diethylethanolamines, N-tert-butyldiethanolamines and N-sulphoethyldiethanolamines; and ii) a compound chosen from $C_{10-30}$ haloalkyls, for example, $C_{12-18}$ haloalkyls, such as bromooctadecanes, chlorooctadecanes, chlorododecyls and bromododecyls.

The at least one cationic associative amphiphilic polymer of formula (I) as disclosed herein is water-soluble or water-dispersible and can substantially increase the viscosity of the aqueous solution in which it is dissolved or dispersed.

For example, the polymer as disclosed herein has a viscosity $\eta_0$ at 27° C. ranging, for example, from 5 to 100 Pa·s, such as from 5 to 70 Pa·s, and further such as from 5 to 60 Pa·s, as an aqueous solution at 7% of the polymer by weight relative to the total weight of the composition, wherein the solution is prepared in the manner described in Example 3 below.

Given its thickening properties and its affinity for a keratin material, this type of cationic associative amphiphilic polymer as disclosed herein may be, for example, suitable for preparing compositions for cosmetic or pharmaceutical use.

The at least one polymer is, for example, present in compositions, such as cosmetic compositions, in an amount ranging, for example, from 0.01% to 40% by weight of solids, such as from 0.05% to 35% by weight of solids, and further such as from 0.05% to 30% by weight of solids, relative to the total weight of the composition.

The compositions, such as cosmetic compositions, comprising at least one polymer as disclosed herein may further comprise, in a cosmetically-acceptable medium, at least one ingredient generally used in this type of composition.

The compositions may, for example, comprise water or a mixture of water and at least one solvent. Non-limiting examples of the at least one solvent include $C_1$–$C_8$ alcohols such as ethanol, isopropanol, tert-butanol and n-butanol; polyols, such as glycerol; glycols such as butylene glycols, isoprene glycols, propylene glycols and polyethylene glycols (for example PEG-8); and polyol ethers.

The compositions as disclosed herein may also comprise at least one additive. Non-limiting examples of the at least one additive include other polymers chosen from fixing and non-fixing, anionic, amphoteric, zwitterionic, nonionic and cationic polymers; surfactants; nacreous agents; opacifiers; organic solvents; fragrances; thickeners; gelling agents; oils and waxes of mineral, plant, animal or synthetic origin; fatty acid esters; colourants; silicones chosen from volatile and non-volatile, organomodified and non-organomodified, cyclicand acyclic, branched and unbranched silicones; mineral particles; organic particles; pigments; fillers; preserving agents; cosmetic active agents; sunscreens; and pH stabilizers.

A person skilled in the art will understand to select this or these optional additional compound(s), and/or the amount thereof, such that the advantageous properties of the composition are not, or are not substantially, adversely affected by the envisaged addition.

The compositions as disclosed herein may be used for treating and caring for facial skin, body skin, mucous membranes (such as the lips), the scalp and/or the hair.

The compositions thus find, for example, application as care compositions for the body or the face; cleansing compositions for the body or the face, such as shower gels, bath gels and makeup removers; makeup compositions for the body or the face, such as foundations, lipsticks, lipcare products, nail varnishes, nailcare products, mascaras and eyeliners; fragrancing compositions; hair compositions, such as hair-colouring compositions and permanent-reshaping compositions for the hair; antisun compositions; cleansing or hair care compositions, such as shampoos, rinse-out or leave-in conditioners, rinse-out compositions to be applied before or after dyeing, bleaching, permanent-waving or straightening the hair; rinse-out compositions to be applied alternatively between the two steps of a permanent-waving and a hair-straightening operation; and hair compositions for holding the hairstyle, such as styling lacquers, gels, mousses and sprays.

The invention is illustrated in greater detail in the examples that follow.

Determination of the Degree of Quaternization (or Content of Quaternized Amine Units)

The halide ion (bromide or chloride) content of the test compound was determined in the following manner.

Depending on the assumed halide content, the following amount of test compound was taken up:

| Assumed % of halide ions | Test sample (g) |
|---|---|
| 50 | 0.1 |
| 10 | 0.5 |
| 6 | 1.5 |
| 1 | 4 |
| 0.05 | 10 |

The test sample was dissolved in 70 ml of demineralized water; 5 ml of $HNO_3$ (6N) were added, and the mixture was stirred and titrated potentiometrically with a silver nitrate solution (0.1 N), with stirring.

A blank test was performed in a similar manner, omitting the test sample and making up volume with distilled water to obtain the same volume as that of the test solution.

The apparatuses used were a Mettler DL 55 memotitrator, and a combined electrode suitable for assay (Mettler DM 141).

The halide content (in meq/g) is given by the following formula:

$$\frac{(Vi - Vo) \times T \times K}{m}$$

in which:
Vo: volume added for the blank test (ml)
Vi: volume added for the assay (ml)
T: titre of the silver nitrate solution (0.1 N)
k: titration factor for the silver nitrate solution
m: mass of the test sample (g).

The degree of quaternization is equal to the ratio between the measured content and the theoretical content for 100% quaternization.

EXAMPLE 1

Polymer According to the Invention

The reaction scheme was as follows:

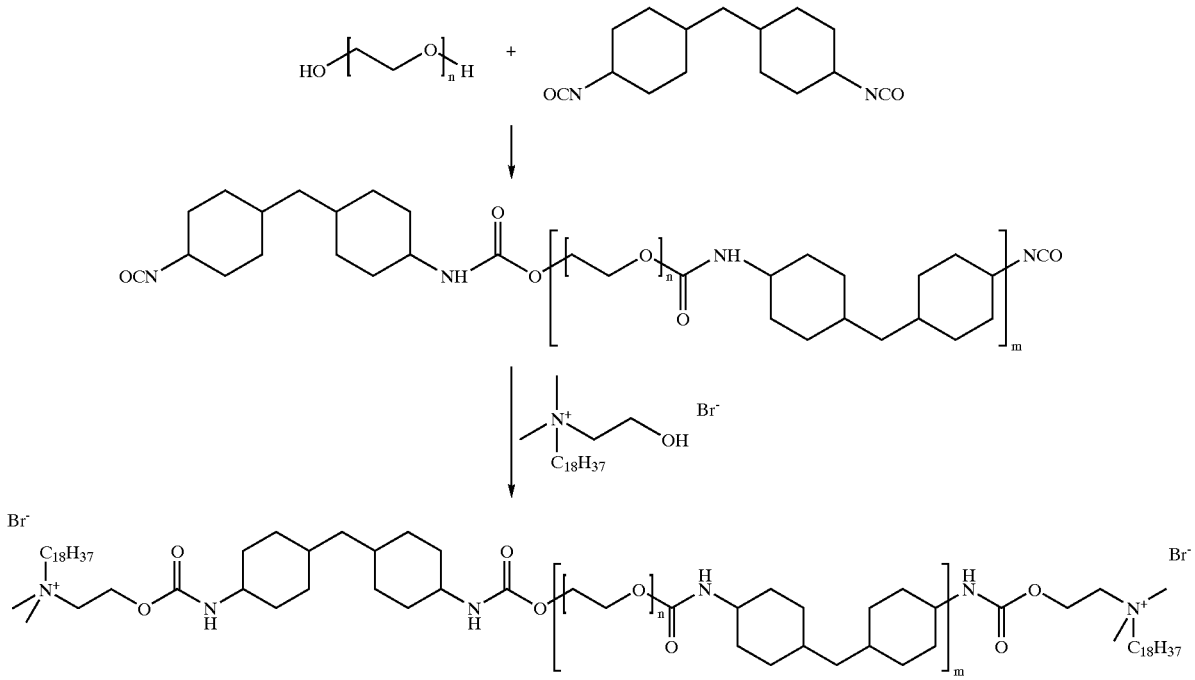

In a first stage, N-stearyl-N,N-dimethylethanolammonium bromide was prepared by quaternizing 1 mol of dimethylaminoethanol with 1 mol of bromooctadecane, as a 50% solution in methyl ethyl ketone, at reflux for 2 hours. The product obtained was diluted with acetone at 20–25° C., filtered off, rinsed with acetone and dried in an oven under vacuum. A product in the form of 95% quaternized nacreous white crystals was obtained (2.30 meq/g; theory=2.43 meq/g).

1,280 g (0.128 mol) of anhydrous poly(ethylene oxide) ($M_n$ 10,000) were dissolved in 840 ml of methyl ethyl ketone, under nitrogen. The mixture was heated to reflux, followed by dropwise addition of 60.4 g (0.23 mol) of methylenedicyclohexyl diisocyanate, and then the mixture was rinsed with 30 ml of methyl ethyl ketone. The reaction medium was refluxed for 8 hours.

38 g (0.114 mol) of N-stearyl-N,N-dimethylethanolammonium bromide were then added, followed by addition of 800 ml of methyl ethyl ketone; the concentration of the medium was then 52%. Refluxing continued for 9 hours.

2,300 ml of methyl ethyl ketone were then added, after which the product was precipitated in two portions, at 70° C., in 8 liters of cold heptane. The product was rinsed with 4 liters of heptane, filtered on a sinter funnel and then dried under vacuum at 40° C. for 24 hours. 1,356 g of a white powder were obtained (98% yield).

The degree of quaternization was 91% (0.06 meq/g; theory=0.066 meq/g).

EXAMPLE 2

Comparative Polymer

Reagents:

| | |
|---|---|
| Polyethylene oxide (PEG)($M_n$ 10,000): | 0.010 mol |
| Methylenedicyclohexyl diisocyanate: | 0.018 mol |
| N,N-dimethylethanolamine: | 0.020 mol |
| Stearyl bromide: | 0.024 mol |
| Tin octanoate (catalyst): | 0.2% |

0.010 mol (100 g) of poly(ethylene oxide) having a number-average mass of 10,000 was dissolved in 105 g of tetrahydrofuran (THF) containing 0.2% tin octanoate (catalyst), followed by dropwise addition of 0.018 mol (4.71 g) of methylenedicyclohexyl diisocyanate. The reaction medium was heated for 15 hours at the reflux temperature of the THF, adding 100 ml of THF after 6 hours. During the reaction, a partial disappearance of the NCO band of the isocyanate was observed by FTIR, along with the appearance of the CO and NH bands for the amide bonds formed. The medium was very viscous and transparent.

0.020 mol (1.78 g) of N,N-dimethylethanolamine was then added and the reaction was continued for 4 hours at the reflux point of the THF, until the NCO band and the OH band of the alcohol completely disappeared.

For the quaternization, 0.024 mol (8 g) of stearyl bromide, i.e., a 20 mol % excess relative to the N,N-dimethylethanolamine, was added to the reaction mixture, followed by addition of 100 g of THF to fluidize the very viscous reaction medium. Heating was continued at the reflux point of the THF for an additional 36 hours.

The polymer obtained was precipitated from petroleum ether, filtered off and dried under vacuum at 40° C. for 24 hours. A crumbly white powder was thus obtained.

A number-average mass of 70,000 and a weight-average mass of 115,000, which corresponds to a polydispersity index of 1.65, was measured by gel permeation chromatography in aqueous medium (calibration with polystyrene).

The degree of quaternization was 30% (0.02 meq/g; theory=0.066 meq/g).

EXAMPLE 3

Viscosity Measurements

An aqueous solution containing 7% by weight of polymer in deionized water was prepared at room temperature, with magnetic stirring for a minimum of 12 hours. The solution was left to stand at 27° C. for a minimum of 12 hours before rheological characterization.

The viscosity measurements were performed using a Haake RS150 controlled-stress rheometer equipped with cone-plate geometry of diameter 35 mm and angle 2°, at a temperature of 27° C.

The sample was subjected to an increasing gradient of shear stresses logarithmically distributed between 0.1 and 1 000 Pa. The duration of the gradient was 2 minutes 30 seconds.

The viscosity values were determined in the first Newtonian region of the rheogram, in which region the viscosity $\eta_0$ ($\eta_0 = \tau/V_c$), also occasionally known as the viscosity at rest, is constant and independent of the applied stress ($\tau$) or the measured shear rate ($V_c$).

The following results were obtained:
polymer of Example 1 (invention): $\eta_0 = 17.0 \pm 0.1$ Pa·s
polymer of Example 2 (comparative): $\eta_0 = 0.6 \pm 0.1$ Pa·s

EXAMPLE 4

Polymer According to the Invention

1) Preparation of N-lauryl-N,N-dimethylethanolammonium bromide of Formula:

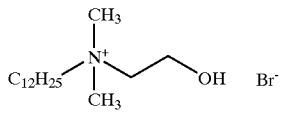

In a first stage, N-lauryl-N,N-dimethylethanolammonium bromide was prepared by quaternizing 1 mol of dimethylaminoethanol with 1 mol of bromododecane, as a 50% solution in methyl ethyl ketone, at reflux for 4 hours. The product obtained was poured into 1 liter of cold heptane, filtered off, rinsed with acetone and dried at 40° C. in an oven under vacuum. A product in the form of 100% quaternized nacreous white crystals was obtained (2.96 meq/g).

2) Preparation of the Polymer 300 g of anhydrous poly(ethylene oxide) ($M_n$ 10,000) were dissolved in 300 ml of methyl ethyl ketone, under nitrogen. The mixture was heated to reflux, followed by dropwise addition of 14.15 g of methylenedicyclohexyl diisocyanate, and the resulting mixture was rinsed with 10 ml of methyl ethyl ketone. The reaction medium was refluxed for 6½ hours.

7.1 g of N-lauryl-N,N-dimethylethanolammonium bromide were then added, followed by addition of 100 ml of methyl ethyl ketone. Refluxing continued for 8 hours.

2 liters of heptane were then added to the product, which then precipitated when cooled to 60° C.

The precipitated product was rinsed with 500 ml of heptane, filtered off on a sinter funnel and then dried under vacuum at 40° C. for 24 hours.

302 g of a white powder were obtained (94% yield). The degree of quaternization was 97% (0.064 meq/g; theory= 0.066 meq/g).

What is claimed is:

1. At least one polymer of formula (I) below:

wherein
R and R', which may be identical or different, are chosen from hydrophobic groups and a hydrogen atom;
X and X', which may be identical or different, are chosen from groups comprising at least one amine functional group chosen from tertiary and quaternary amine functional groups, optionally bearing at least one hydrophobic group;
L and L', which may be identical or different, are each chosen from groups derived from diisocyanate;
Y is chosen from hydrophilic groups;
r is an integer ranging from 1 to 100;
m is a number ranging from 1 to 1,000,
wherein the polymer comprises at least one amine functional group chosen from protonated and quaternized amine functional groups and at least one hydrophobic group, it being understood that the content of the quaternized amine unit is at least 85%.

2. The at least one polymer according to claim 1, wherein r is an integer ranging from 1 to 50.

3. The at least one polymer according to claim 2, wherein r is an integer ranging from 1 to 25.

4. The at least one polymer according to claim 1, wherein the content of the quaternized amine unit ranges from 87% to 100%.

5. The at least one polymer according to claim 4, wherein the content of the quarternized amine unit ranges from 88% to 99%.

6. The at least one polymer according to claim 1, wherein:
R and R', which may be identical or different, are chosen from hydrophobic groups; and
X and X', which may be identical or different, are chosen from groups comprising at least one quaternary amine functional group.

7. The at least one polymer according to claim 1, wherein the number-average molecular mass of the at least one polymer ranges from 10,000 to 60,000.

8. The at least one polymer according to claim 7, wherein the number-average molecular mass of the at least one polymer ranges from 15,000 to 55,000.

9. The at least one polymer according to claim 8, wherein the number-average molecular mass of the at least one polymer ranges from 20,000 to 50,000.

10. The at least one polymer according to claim 1, wherein in the definition of X and X', the at least one hydrophobic group is chosen from radicals and polymeric groups comprising at least one hydrocarbon-based chain chosen from linear and branched, saturated and unsaturated hydrocarbon-based chains, and radicals comprising at least one chain chosen from perfluoro and silicone chains.

11. The at least one polymer according to claim 1, wherein in the definition of R and R', the hydrophobic groups are chosen from radicals and polymeric groups comprising at least one hydrocarbon-based chain chosen from linear and branched, saturated and unsaturated hydrocarbon-based chains, and radicals comprising at least one chain chosen from perfluoro and silicone chains.

12. The at least one polymer according to claim 10, wherein the at least one hydrocarbon-based chain comprises at least one hetero atom.

13. The at least one polymer according to claim 11, wherein the at least one hydrocarbon-based chain comprises at least one hetero atom.

14. The at least one polymer according to claim 12, wherein the at least one hetero atom is chosen from P, O, N and S.

15. The at least one polymer according to claim 13, wherein the at least one hetero atom is chosen from P, O, N and S.

16. The at least one polymer according to claim 10, wherein the at least one hydrophobic group is chosen from hydrocarbon-based radicals comprising at least 10 carbon atoms.

17. The at least one polymer according to claim 11, wherein the hydrophobic groups are chosen from hydrocarbon-based radicals comprising at least 10 carbon atoms.

18. The at least one polymer according to claim 16, wherein the at least one hydrophobic group is chosen from hydrocarbon-based radicals comprising from 10 to 30 carbon atoms.

19. The at least one polymer according to claim 17, wherein the hydrophobic groups are chosen from hydrocarbon-based radicals comprising from 10 to 30 carbon atoms.

20. The at least one polymer according to claim 18, wherein the at least one hydrophobic group is chosen from hydrocarbon-based radicals comprising from 12 to 30 carbon atoms.

21. The at least one polymer according to claim 19, wherein the hydrophobic groups are chosen from hydrocarbon-based radicals comprising from 12 to 30 carbon atoms.

22. The at least one polymer according to claim 20, wherein the at least one hydrophobic group is chosen from hydrocarbon-based radicals comprising from 18 to 30 carbon atoms.

23. The at least one polymer according to claim 21, wherein the hydrophobic groups are chosen from hydrocarbon-based radicals comprising from 18 to 30 carbon atoms.

24. The at least one polymer according to claim 16, wherein the at least one hydrophobic group is chosen from decyl, dodecyl, myristyl, palmityl and stearyl groups.

25. The at least one polymer according to claim 17, wherein the hydrophobic groups are chosen from decyl, dodecyl, myristyl, palmityl and stearyl groups.

26. The at least one polymer according to claim 10, wherein the at least one hydrophobic group is polybutadiene.

27. The at least one polymer according to claim 11, wherein the hydrophobic groups are polybutadiene.

28. The at least one polymer according to claim 1, wherein the groups X and X' represent one of the following formulae:

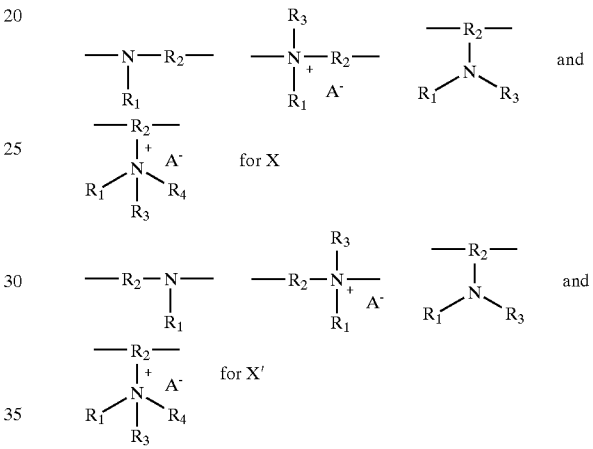

wherein:
R$_2$ is a radical chosen from linear and branched alkylene radicals comprising from 1 to 20 carbon atoms, and arylene radicals, wherein at least one of the carbon atoms in said radicals is optionally substituted with at least one hetero atom chosen from N, S, O and P;

R$_1$, R$_3$ and R$_4$, which may be identical or different, are each a radical chosen from linear and branched C$_1$–C$_{30}$ alkyls, linear and branched C$_1$–C$_{30}$ alkenyl radicals, and aryl radicals, wherein at least one of the carbon atoms in said radicals is optionally substituted with at least one hetero atom chosen from N, S, O and P; and A$^-$ is chosen from physiologically-acceptable counterions.

29. The at least one polymer according to claim 28, wherein, in defining R$_2$, the linear and branched alkylene radicals comprise at least one ring chosen from saturated and unsaturated rings.

30. The at least one polymer according to claim 1, wherein the groups L and L' are chosen from groups of the following formula:

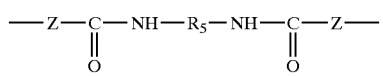

wherein:
Z is a radical chosen from —O—, —S— and —NH—; and $R_5$ is a divalent alkylene radical chosen from linear, branched and cyclic, saturated and unsaturated divalent alkylene radicals comprising from 1 to 20 carbon atoms.

31. The at least one polymer according to claim 30, wherein the divalent alkylene radical comprises at least one hetero atom chosen from N, S, O and P.

32. The at least one polymer according to claim 1, wherein Y is chosen from hydrophilic groups comprising at least one functional group comprising at least one labile hydrogen.

33. The at least one polymer according to claim 32, wherein the at least one functional group comprising at least one labile hydrogen is chosen from alcohol, primary amine, secondary amine and thiol functional groups.

34. The at least one polymer according to claim 1, wherein Y is chosen from at least one of ethylene glycol, diethylene glycol, propylene glycol, polyethers, sulphonated polyesters, and sulphonated polyamides.

35. The at least one polymer according to claim 34, wherein Y is chosen from at least one of poly(ethylene oxide) and poly(propylene oxide).

36. The at least one polymer according to claim 1, wherein the viscosity $\eta_0$ at 27° C. ranges from 5 to 100 Pa·s, as an aqueous solution at 7% of the at least one polymer by weight relative to the total weight of the solution.

37. The at least one polymer according to claim 36, wherein the viscosity $\eta_0$ at 27° C. ranges from 5 to 70 Pa·s as an aqueous solution at 7% of the at least one polymer by weight relative to the total weight of the solution.

38. The at least one polymer according to claim 37, wherein the viscosity $\eta_0$ at 27° C. ranges from 5 to 60 Pa·s as an aqueous solution at 7% of the at least one polymer by weight relative to the total weight of the solution.

39. A process for preparing at least one polymer, comprising reacting a quaternized amine derivative with a diisocyanate prepolymer; wherein the at least one polymer is of formula (I) below:

R-X-[L-(Y)$_m$]$_r$-L'-X'-R'     (I)

wherein
R and R', which may be identical or different, are chosen from hydrophobic groups and a hydrogen atom;
X and X', which may be identical or different, are chosen from groups comprising at least one amine functional group chosen from tertiary and quaternary amine functional groups, optionally bearing at least one hydrophobic group;
L and L', which may be identical or different, are each chosen from groups derived from diisocyanate;
Y is chosen from hydrophilic groups;
r is an integer ranging from 1 to 100;
m is a number ranging from 1 to 1,000,
wherein the polymer comprises at least one amine functional group chosen from protonated and quaternized amine functional groups and at least one hydrophobic group, it being understood that the content of the quaternized amine unit is at least 85%.

40. The process according to claim 39, wherein the diisocyanate prepolymer is obtained by coupling a prepolymer comprising at least one functional group comprising at least one labile hydrogen with a diisocyanate of the formula:

O=C=N—R$_5$—N=O wherein $R_5$ is a divalent alkylene radical chosen from linear, branched and cyclic, saturated and unsaturated divalent alkylene radicals comprising from 1 to 20 carbon atoms, optionally comprising at least one hetero atom chosen from N, S, O and P.

41. The process according to claim 40, wherein the diisocyanate is chosen from methylenediphenyl diisocyanates, methylenedicyclohexyl diisocyanates, isophorone diisocyanates, toluene diisocyantes, naphthalene diisocyanates, butane diisocyanates and hexane diisocyanates.

42. The process according to claim 39, wherein the quaternized amine derivative comprises at least one unit comprising a quaternized amine functional group and at least one labile hydrogen.

43. The process according to claim 42, wherein the quaternized amine derivative is chosen from the products of a reaction between:
i) a compound chosen from N-methylethanolamines, N-methyldiethanolamines, N,N-dimethylethanolamines, N,N-diethylethanolamines, N-tert-butyldiethanolamines and N-sulphoethyldiethanolamines; and
ii) a compound chosen from C$_{10-30}$ haloalkyls.

44. At least one thickener polymer of formula (I) below:

R-X-[L-(Y)$_m$]$_r$-L'-X'-R'     (I)

wherein
R and R', which may be identical or different, are chosen from hydrophobic groups and a hydrogen atom;
X and X', which may be identical or different, are chosen from groups comprising at least one amine functional group chosen from tertiary and quaternary amine functional groups, optionally bearing at least one hydrophobic group;
L and L', which may be identical or different, are each chosen from groups derived from diisocyanate;
Y is chosen from hydrophilic groups;
r is an integer ranging from 1 to 100;
m is a number ranging from 1 to 1,000,
wherein the polymer comprises at least one amine functional group chosen from protonated and quaternized amine functional groups and at least one hydrophobic group, it being understood that the content of the quaternized amine unit is at least 85%; and wherein the polymer is effective as a thickener.

45. A composition comprising at least one polymer of formula (I) below:

R-X-[L-(Y)$_m$]$_r$-L'-X'-R'     (I)

wherein
R and R', which may be identical or different, are chosen from hydrophobic groups and a hydrogen atom;
X and X', which may be identical or different, are chosen from groups comprising at least one amine functional group chosen from tertiary and quaternary amine functional groups, optionally bearing at least one hydrophobic group;
L and L', which may be identical or different, are each chosen from groups derived from diisocyanate;
Y is chosen from hydrophilic groups;
r is an integer ranging from 1 to 100;
m is a number ranging from 1 to 1,000,
wherein the polymer comprises at least one amine functional group chosen from protonated and quaternized amine functional groups and at least one hydrophobic group, it being understood that the content of the quaternized amine unit is at least 85%.

46. The composition according to claim 45, comprising, in a cosmetically-acceptable medium, the at least one polymer, wherein the at least one polymer is in an amount ranging from 0.01% to 40% by weight of solids, relative to the total weight of the composition.

47. The composition according to claim 46, wherein the at least one polymer is in an amount ranging from 0.05% to 35% by weight of solids, relative to the total weight of the composition.

48. The composition according to claim 47, wherein the at least one polymer is in an amount ranging from 0.05% to 30% by weight of solids, relative to the total weight of the composition.

49. The composition according to claim 45, wherein the composition is chosen from care compositions, cleansing compositions, and makeup compositions for body and/or face; fragrancing compositions; hair compositions; anti-sun compositions; cleansing and care compositions for hair; and hair compositions for holding the hairstyle.

50. The composition according to claim 49, wherein the cleansing compositions for body and/or face are chosen from shower gels, bath gels, and makeup removers.

51. The composition according to claim 49, wherein the makeup compositions for body and/or face are chosen from foundations, lipsticks, lip care products, nail varnishes, nail care products, mascaras and eyeliners.

52. The composition according to claim 49, wherein the hair compositions are chosen from hair-coloring compositions and permanent-reshaping compositions for hair.

53. The composition according to claim 49, wherein the cleansing and care compositions for hair are chosen from shampoos, rinse-out conditioners, leave-in conditioners, rinse-out compositions to be applied before or after dyeing, bleaching, permanent-waving or straightening the hair and to be applied between the two operations of a permanent-waving and hair-straightening.

54. The composition according to claim 49, wherein the hair compositions for holding the hairstyle are chosen from styling lacquers, gels, mousses and sprays.

55. A process for thickening a composition comprising including in the composition at least one polymer as a thickener, wherein the at least one polymer is of formula (I) below:

$$R\text{-}X\text{-}[L\text{-}(Y)_m]_r\text{-}L'\text{-}X'\text{-}R' \quad \text{(I)}$$

wherein
- R and R', which may be identical or different, are chosen from hydrophobic groups and a hydrogen atom;
- X and X', which may be identical or different, are chosen from groups comprising at least one amine functional group chosen from tertiary and quaternary amine functional groups, optionally bearing at least one hydrophobic group;
- L and L', which may be identical or different, are each chosen from groups derived from diisocyanate;
- Y is chosen from hydrophilic groups;
- r is an integer ranging from 1 to 100;
- m is a number ranging from 1 to 1,000, wherein the polymer comprises at least one amine functional group chosen from protonated and quaternized amine functional groups and at least one hydrophobic group, it being understood that the content of the quaternized amine unit is at least 85%.

56. At least one polymer of formula (I) below:

$$R\text{-}X\text{-}[L\text{-}(Y)_m]_r\text{-}L'\text{-}X'\text{-}R' \quad \text{(I)}$$

wherein
- R and R', which may be identical or different, are chosen from hydrophobic groups and a hydrogen atom;
- X and X', which may be identical or different, are chosen from groups comprising at least one amine functional group chosen from tertiary and quaternary amine functional groups, optionally bearing at least one hydrophobic group;
- L and L', which may be identical or different, are each chosen from groups derived from diisocyanate;
- Y is chosen from hydrophilic groups;
- r is an integer ranging from 1 to about 100;
- m is a number ranging from 1 to about 1,000, wherein the polymer comprises at least one amine functional group chosen from protonated and quaternized amine functional groups and at least one hydrophobic group, it being understood that the content of the quaternized amine unit is at least about 85%.

* * * * *

UNITED STATES PATENT AND TRADEMARK OFFICE
CERTIFICATE OF CORRECTION

PATENT NO.    : 6,939,938 B2
DATED         : September 6, 2005
INVENTOR(S)   : Sylvie Benard et al.

It is certified that error appears in the above-identified patent and that said Letters Patent is hereby corrected as shown below:

<u>Title page</u>,
Item [75], Inventors, "Sylvi" should read -- Sylvie --.

<u>Column 14</u>,
Line 7, "diisocyantes," should read -- diisocyanates, --.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,939,938 B2  Page 1 of 1
APPLICATION NO. : 10/347414
DATED : September 6, 2005
INVENTOR(S) : Sylvie Benard et al.

It is certified that error appears in the above-identified patent and that said Letters Patent is hereby corrected as shown below:

In claim 40, column 13, line 65, the formula "O=C=N-$R_5$-N=O" should read --O=C=N-$R_5$-N=C=O--.

Signed and Sealed this

Thirteenth Day of January, 2009

JON W. DUDAS
*Director of the United States Patent and Trademark Office*